United States Patent [19]
Cusack et al.

[11] Patent Number: 5,314,441
[45] Date of Patent: May 24, 1994

[54] DISPOSABLE SLICING LANCET ASSEMBLY

[75] Inventors: Robert Cusack, Edison; Robert Samo, Lakewood, both of N.J.

[73] Assignee: International Technidyne Corporation, Edison, N.J.

[21] Appl. No.: 962,284

[22] Filed: Oct. 16, 1992

[51] Int. Cl.$^5$ ............................................ A61B 17/32
[52] U.S. Cl. ................................................... 606/182
[58] Field of Search ......................... 606/182, 181, 183

[56] References Cited

U.S. PATENT DOCUMENTS

| 4,705 | 8/1846 | Tiemann | 606/183 |
|---|---|---|---|
| 2,823,677 | 2/1958 | Hein, Jr. | |

FOREIGN PATENT DOCUMENTS

| 2841174 | 4/1979 | Fed. Rep. of Germany | 606/182 |
|---|---|---|---|
| 3009700 | 10/1980 | Fed. Rep. of Germany | 606/182 |
| 3156 | 10/1825 | France | 606/181 |
| 2327755 | 5/1977 | France | 606/182 |

*Primary Examiner*—Tamara L. Graysay
*Attorney, Agent, or Firm*—Plevy & Associates

[57] ABSTRACT

A lancet device uses a planar blade that implements an incision in the skin of a patient using a slicing action. There is a blade support arm pivotably secured within a hollow housing. The pivot connection between the blade support arm and the housing is formed by a pivot pin which extends from the housing and is positioned in a slot receptacle formed on the blade support arm. The pivot pin is free to reciprocally move within the slot receptacle as the blade support arm pivot about the pivot pin. The rotation of the blade support arm about the pivot pin is implemented by a bias spring. The path traversed by the blade support arm as it pivots is controlled by a groove located on the interior surface of the housing which engages a projection that extends from the blade support arm. As such, when the support arm pivots from a first position to a second position, the projection on the blade support arm traverses the groove in the housing. The action of the projection of the blade support arm following the groove in the housing causes the slot receptacle on the blade support arm to reciprocate. Consequently, the blade is caused to reciprocate within the housing as it rotates with the blade support arm, wherein the blade exits the housing, implements an incision and is again retracted into the housing traversing a "tear drop" shaped path.

18 Claims, 7 Drawing Sheets

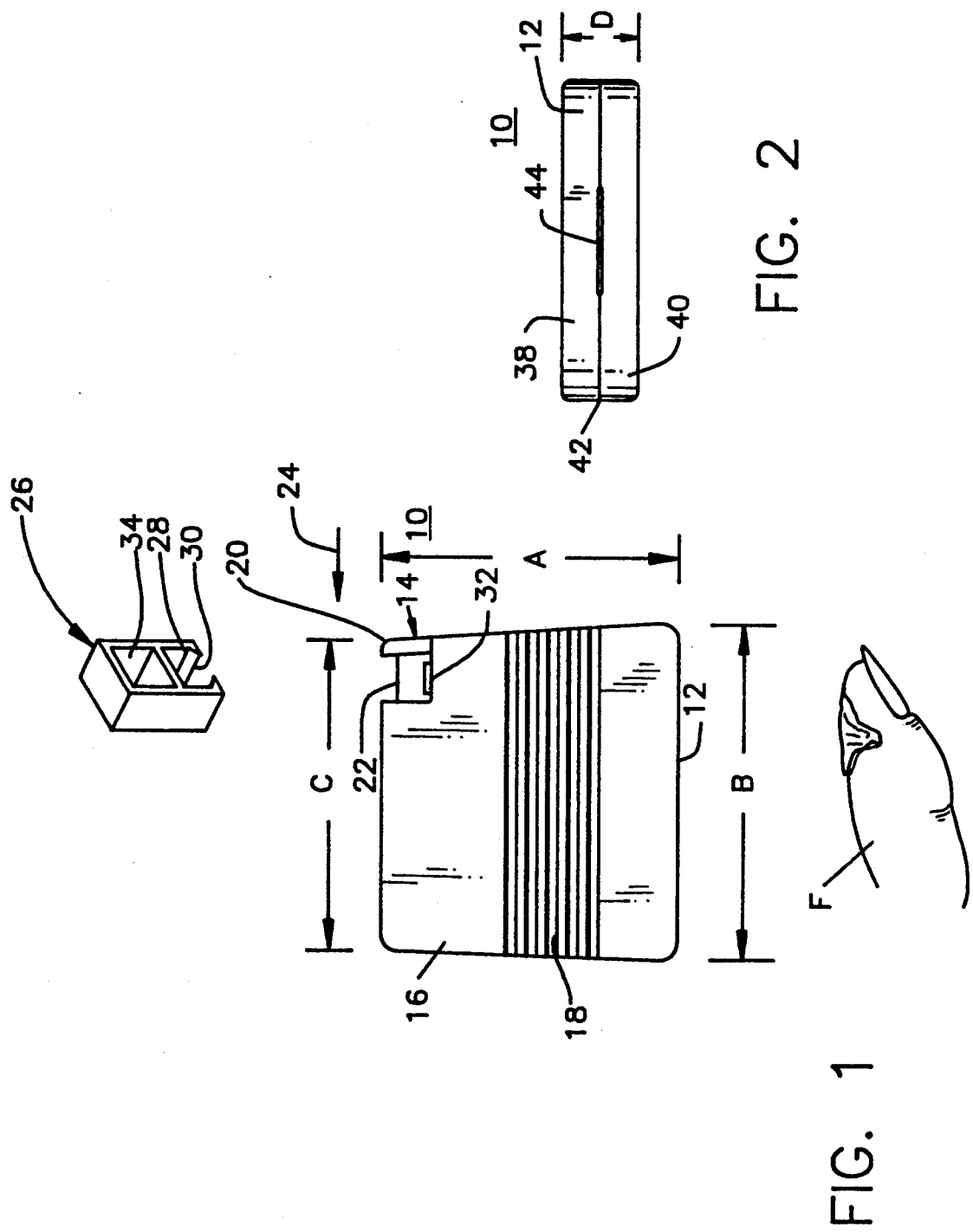

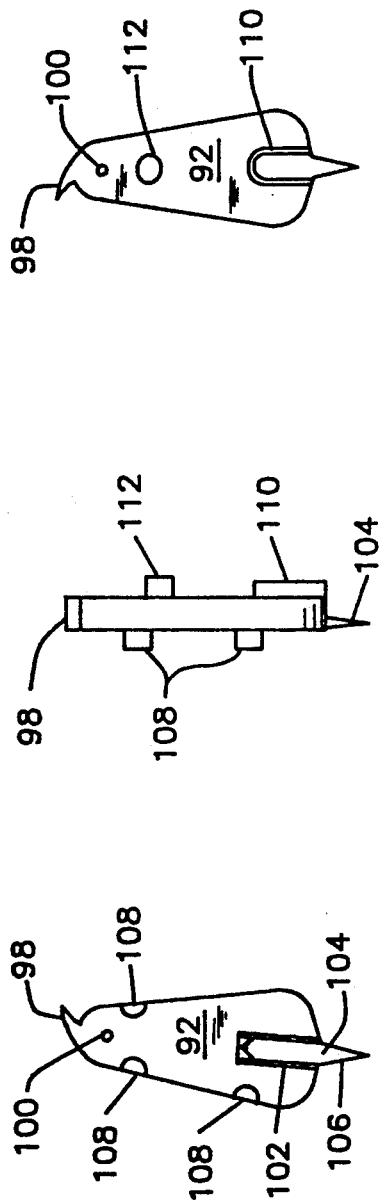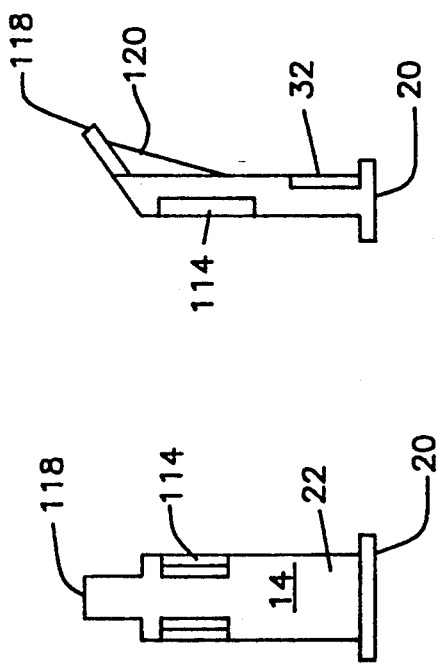

DISPOSABLE SLICING LANCET ASSEMBLY

FIELD OF INVENTION

The present invention relates to disposable single-use lancet devices used to cause bleeding in a patent, and more particularly to such disposable lancet devices that create an incision implementing a slicing action to provide a clean deep incision with a reduction in trauma to tissue surrounding the incision and with reduced pain to the patient.

BACKGROUND OF THE INVENTION

Blood samples are drawn routinely from patients for use in numerous types of blood tests. The blood needed for many tests is conventionally drawn by creating a small incision in the patient's skin. Typically, such incisions are made on the patient's fingertip, however, with such patients as neonates or persons with poor circulation, the incision can be made in alternate areas such as the foot, arm, leg, etc. Typically, the device used to create the needed incision in the patient is a mechanical lancet device. Such lancet devices conventionally employ a cutting blade spring loaded within a housing. The housing is placed against a patient's skin and the blade is released. The potential energy stored within the spring bias of the blade then causes the blade to exit the housing and to create the needed incision in the patient's skin. The advantages of such mechanical lancet devices is that uniform incisions can be made providing good control over the location, depth and sterility of the incision. Furthermore, such mechanical lancet devices often prevent the patient from seeing the often unsettling scene of his or her skin actually being cut.

In the development of the art for mechanical lancet devices, many different designs have been created. The most modern of the designs typically are disposable, having retractable blades and other operations that prevent their reuse after a single incision has been made. Another common feature to many prior art lancet devices is that they made incisions using a plunge cut, that is the cutting blade is plunged through the skin traveling perpendicular to the skin and the size of the incision matches the size of the cutting blade. In U.S. Pat. No. 5,133,730 issued on Jul. 28, 1992 to Biro, entitled DISPOSABLE RETRACTABLE FINGER STICK DEVICE AND METHOD FOR MAKING THE SAME and assigned to International Technidyne Corporation the assignee herein, a sharp blade on a pivot arm is spring biased to move out of and then reenter a housing via an orifice in the housing to incise a patient's skin. Although, the blade is positioned on a pivot arm the blade is directed into the skin of the patient relatively perpendicular to the surface of the skin. The shape of the blade helps the blade enter the skin and make the needed incision.

Lancet devices that create plunge cut are exemplified by U.S. Pat. No. 3,760,809 to Cambell, Jr. entitled SURGICAL LANCET HAVING CASING and U.S. Pat. No. 4,553,541 to Burns entitled AUTOMATIC RETRACTABLE LANCET ASSEMBLY. In both references, the blades are plunged into the skin at an angle substantially perpendicular to the skin. When creating an incision for obtaining a blood sample, it is desirable to create a fairly deep cut so that a good blood flow will result from the incision. However, when using certain prior art lancet devices of the type that utilize a downward thrust to provide a cut pointed blades are typically used to facilitate the cut. Pointed blades create a V-shaped incision down through the skin of the patient. Consequently, the widest region of the incision is on the surface of the skin, while the narrowest region of the incision coincides the deepest point of the incision. Since the narrowest point of the cut is also the deepest point of the cut, a relatively deep incision must be made to ensure enough capillaries are severed to achieve the necessary bleeding.

Another disadvantage associated with plunge cut lancet devices is that they are painful. As will be recognized by any person skilled in the art, a plunge incision is more traumatic than an incision made by a scalpel slice. As such, there is less pain associated with a slice incision than with a plunge incision. Slice incisions as indicated are less intrusive and heal more readily. Additionally, incisions produced by the above-noted prior art devices are made by a downward thrust into the skin. As such, there may be a problem of excessive force being applied to the skin, which can cause skin tissue surrounding the incision to be damaged. Generally, only a small amount of downward force is required to make the incision. However, when the operator actuates the device, his hand may exert an additional, and often excessive, downward force. Thus, the guillotine-like, vertical thrust of the blade, coupled with excessive downward force exerted by the operator may cause damage to the skin and cause skin tissue juices to mix with blood, thereby producing improper blood samples. In general, most plunge type lancet devices depend on spring force for incision and retraction and are often unreliable in the accuracy and repeatability of the depth of the cut due to the wide range of skin toughness encountered in normal populations.

In the prior art, slice action devices are typically used to implement incisions which permit the observation of the bleeding times, wherein bleeding time is defined as the time between implementing the incision and the moment when the bleeding stops. Such slice action devices are exemplified by U.S. Pat. No. 4,064,817 to Reno, entitled DEVICE FOR MAKING PRECISE INCISIONS FOR BLEEDING TIME TESTING AND THE LIKE and U.S. Pat. No. 4,157,086 to Maiorano et al. entitled APPARATUS FOR IMPLEMENTING A STANDARDIZED SKIN INCISION. In both references, blades are causes to slice across a patient's skin causing a elongated incision. The disadvantages of the Maiorano and Reno references is that they both create cuts that are much longer than they are deep. As such, the resulting cut is inappropriate for use on a fingertip or other body part with a small surface area. Furthermore, both the Maiorano and Reno references disclose reusable devices which presents a sterility problem and a hazard of contamination to patients.

The "APPARATUS FOR IMPLEMENTING A STANDARDIZED SKIN INCISION" disclosed in U.S. Pat. No. 4,643,189, and issued to Michael Mintz, and assigned to the assignee herein shows a slice action cutter that creates a rectangular incision. The Mintz patent includes a housing having an internal hollow and a base containing an elongated slot. The internal hollow contains a moveable pivot arm having a blade extending form one end. The pivotal movement of the pivot arm is controlled by a cam having three distinct shaped sections. The cam controls the path of the cutting edge as it implements the incision. As the pivot arm follows the cam, the three distinctly shaped regions of the cam cause the cutting blade to exit the housing, create the incision and return into the housing, respectively. The incision created is rectilinear thereby creating an optimal incision for a bleed time test. The cut provided is implemented by the blade first depending from the slot and plunging into the skin and then traversing the skin and then retracting from the skin back into the housing.

It is, therefore, an objective of the present invention to provide a disposable, single-use lancet that utilizes a slicing action, wherein a short deep incision can be affected on a patient's fingertip or another body part with a reduction in both trauma and pain incurred in the patient as a result of the incision.

SUMMARY OF THE INVENTION

The present invention is a lancet device for implementing an incision through the skin of a patient, thereby allowing for a blood sample to be obtained. The present invention lancet device uses a planar blade that implements the needed incision using a slicing action. By using a slicing action instead of a plunge cut, the blade can create a cleaner, deeper, less traumatic cut which provides the needed bleeding yet heals quickly. In the present invention lancet there is a blade support arm pivotably secured within a hollow housing. The pivot connection between the blade support arm and the housing is formed by a pivot pin which extends from the housing and enters a slot receptacle formed on the blade support arm. Since the slot receptacle is larger than the pivot pin, the pivot pin is free to reciprocally move within the slot receptacle as the blade support arm pivots about the pivot pin. The rotation of the blade support arm around the pivot pin is urged by the presence of a spring bias. Furthermore, the path traversed by the blade support arm, as it pivots around the pivot pin, is controlled by employing a groove formed on the interior surface of the housing. The groove engages a projection that extends from the blade support arm. Consequently, as the support arm pivots from a first position to a second position, the projection on the blade support arm traverses the groove in the housing. The action of the projection of the blade support arm following the groove in the housing, causes the slot receptacle on the blade support arm to rise and fall relative to the engaged pivot pin. Consequently, the blade is caused to rise and fall within the housing as it rotates with the blade support arm.

In the present invention lancet device, the groove formed in on the interior surface of the housing includes a substantially linear section. As the projection on the blade support arm traverses the linear portion of the groove, the blade is caused to traverse a tear shaped cutting path. As the blade moves along its tear-shaped path the blade exits the housing, causes the slice incision and is again retracted into the housing. The blade support arm is positioned between two parallel opposing walls within a hollow housing. Spacers are provided between the blade support arm and the interior walls of the housing. As such, the blade support arm contacts both opposing walls within the housing as the blade support arm pivots from a first position to a second position. The contact between the blade support arm and the opposing surfaces within the housing acts to confine and stabilize the movement of the blade support arm and the blade within a single desired plane, thereby ensuring a straight and even incision.

BRIEF DESCRIPTION OF DRAWINGS

For a better understanding of the present invention, reference is made to the following description of an exemplary embodiment thereof, considered in conjunction with the accompanying drawings, in which:

FIG. 1 is a side view of one preferred embodiment of the present invention shown in conjunction with a patient's fingertip for describing the operation of the present invention;

FIG. 2 is a bottom view of the present invention;

FIG. 5A is a front view of one embodiment for a pivot arm and cutting edge to be employed within the present invention;

FIG. 5B is a side view of the pivot arm depicted in FIG. 5A;

FIG. 5C is a rear view of the pivot arm depicted in FIG. 5A;

FIG. 6A is a top view of one embodiment for a trigger mechanism to be employed within the present invention;

FIG. 6B is a side view of the trigger mechanism depicted in FIG. 6A;

DETAILED DESCRIPTION OF THE INVENTION

Figure 3B:
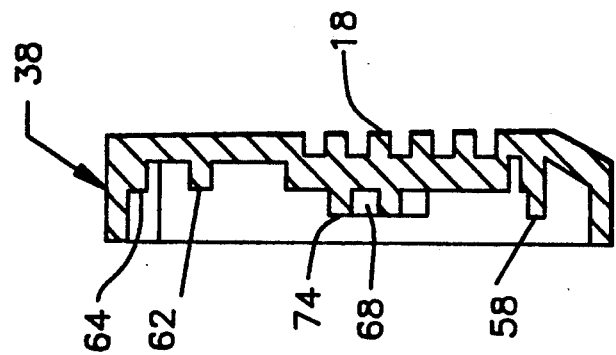
FIG. 3B is a cross-sectional view of the housing half shown in FIG. 3A viewed along section line 3B—3B.

Preferring to FIG. 1, there is shown the present invention lancet device 10 having made an incision on the fingertip F of a patient. When making an incision, the bottom edge 12 of the lancet device 10 is placed against the skin of a patient. Although, the present invention lancet device 10 is preferably held against a patient's fingertip F, as shown, the lancet device 10 can be positioned against any appropriate area of skin on a patient such as the heal of a neonate. Once the lancet device 10 is properly positioned on a patient, an incision is made through the skin of the patient by a cutting blade which is activated by depressing the trigger plunger 14, as will be later explained. Prior to depressing the trigger plunger 14, the cutting blade is completely contained within the housing 16 of the lancet device 10 and is not exposed in any manner until the trigger plunger 14 is engaged. When the trigger plunger 14 is engaged, the cutting blade is projected out of, and traverses across, a slot formed within the bottom edge 12 of the lancet device 10. The cutting blade traverses the slot with a simultaneous vertical and horizontal movement thereby causing an incision with a slicing action.

In the shown embodiment, the housing 16 of the lancet device 10 bears a plurality of grooves 18 on its exterior for enhancing the ease at which the lancet device 10 may be gripped as well as for aesthetic purposes. The portions of the trigger plunger 14 extending from the assembled housing 16 of the lancet device 10 includes a finger tab 20 and a pushrod 22. As will be later described, the lancet device 20 is activated by pushing the finger tab 20 in and toward the housing 16 as indicated by arrow 24. The trigger plunger 14 is supported internally in the upper portion of the housing 16 in a channel. In order to prevent the inadvertent operation of the lancet device 10, a safety clip 26 is employed. The clip 26 has a U-shaped lower region 28 or similar shaped slot receptacle which removably embraces the portion of the pushrod 22 that extends from the housing 16. The clip 26 abuts against the finger tab 20 on one side and the housing 16 on the other, preventing the trigger plunger 14 from being advanced into the housing 16. The clip 26 has locking tabs 30 extending inwardly on either side of the U-shaped lower region 28. The locking tabs 30 engage small indentations 32 formed into the side edges of the pushrod 22. As such, the clip 26 physically engages the pushrod 22 preventing its inadvertent removal from pushrod 22. Furthermore, the clip 26 includes a gripping region 34 that extends above U-shaped lower region 28. The gripping region 34 providing a means through which a user may grasp and remove the clip 26 from the lancet device 10.

The preferred embodiment of the present invention lancet 10 has a height A of approximately 30 mm, a bottom width B of approximately 32 mm, a top width C of approximately 30 mm and a depth D of approximately 11 mm. As will be recognized by a person skilled in the art, the dimensions may vary, but for the purpose of economizing materials, the lancet device 10 would typically be as small as can readily be safely and effectively manipulated by the hands of a user. The above described operation as well as the appearance of the housing, the trigger and so on are generally shown in U.S. Pat. No. 4,643,189.

Referring to FIG. 2, the bottom edge 12 of the lancet device 10 is shown. From this view, it can be seen that the housing 16 of the lancet device 10 is preferably comprised of two mating halves, a first half 38, and a second half 40 which are joined together along a common seam line 42. The housing halves 38,40 may be joined using any known technique such as gluing, fusing, peg and hole construction or the like. In the center of the bottom edge 12 of the lancet device 10 is an elongated slot 44. It is through this slot 44 that a cutting blade is projected to cause an incision, as will be explained.

Figure 3A:
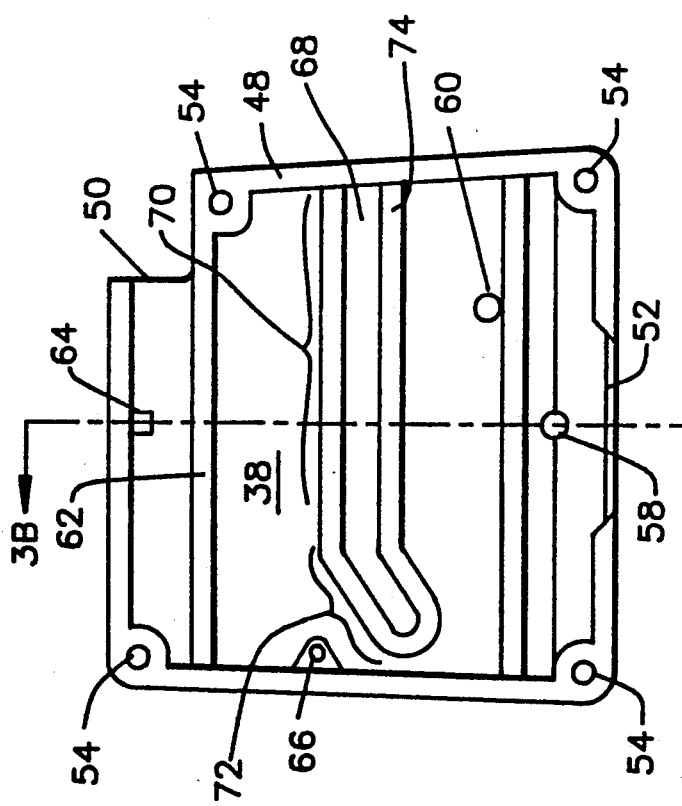
FIG. 3A is a side view of the interior of half the housing of the present invention.

Referring to FIGS. 3A and 3B there is shown the interior of the first half 38 of the lancet housing 16 and a cross sectional view of that first housing half 38 respectively. The first half 38 of the housing contains the gripping grooves 18 molded on its exterior surface. The interior surface of the first housing half 38 is for the most part hollow. The periphery of rear housing half 38 is defined by a edge wall 48 that forms the side surfaces of the lancet device 10 when joined with the second housing half 40. The edge wall 48 is not continuously formed around the first housing half 38, but rather is disrupted in one corner so as to form one half of the aperture 50 through which the trigger plunger 14 will eventually pass. Additionally, the edge wall 48 has a reduced section 52 along its bottom edge. The reduced section 52 acts to form one half of the elongated slot 44 through which a cutting edge will eventually pass.

Positioned at four points proximate the four corners of the first housing half 38 are formed dowel holes 54. The dowel holes 54 join with dowel pins on the second housing half 40 when the first housing half 38 and the second housing half 40 are joined. Two pins extend upwardly from the inner surface of the first housing half 38. The first pin is a pivot pin 58 positioned a point directly above the center of the reduced section 52 on the bottom surface of the first housing half 38. The pivot pin 58 extends up from the inner surface of the rear housing half 38 to a point approximately one-half as high as the edge wall 48 which defines the periphery of the first housing half 38. The second pin is a spacing pin 60 which extends in height well above the height of the edge wall 48. The spacing pin 60 contacts the inner surface of the opposing second housing half 40 thereby preventing the hollow with an assembled housing 16 from being compressed by the force of a user's hand when gripping the exterior of the housing 16. The pin 60 further provides a positive abutive means which operates to limit the travel of pivot arm 92.

Positioned at the upper end of the first housing half 38 is a support track 62. As will be later explained, the support track 62 supports and guides the movement of the trigger plunger 14 in the housing 16. A stop tab 64 is positioned at a point above the support track 62. The stop tab 64 engages the trigger plunger 14, preventing the trigger plunger from being removed from the housing. In the center of the rear housing half 38, is formed a cam guide channel 68. The cam guide channel 68 is a groove in the rear housing half 38 that is generally J-shaped or doglegged in its geometry having a long straight section 70 traveling in the horizontal that turns into a short curved descending section 72. The cam guide channel 68 is preferably formed from a continuous flange wall 74 that extends above the inner surface of the first housing half 38 and defines the limits of the cam guide channel 68. Furthermore, a spring anchor aperture 66 is positioned between the cam guide channel 68 and the support track 62. As will be later explained, the spring anchor aperture 66 acts as the point of attachment between a spring and the housing 16.

Figure 4B:
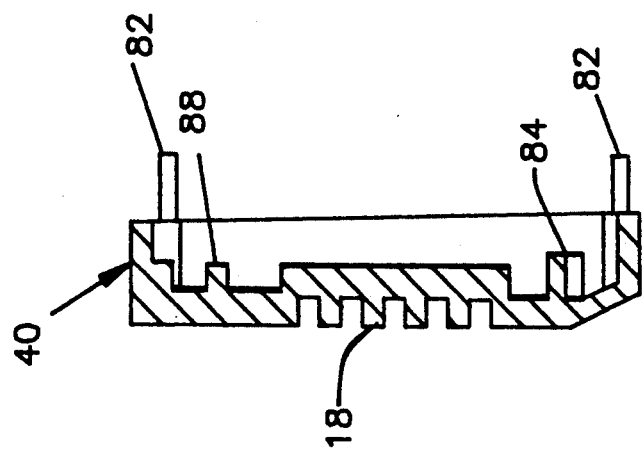
FIG. 4B is a cross-sectional view of the housing half shown in FIG. 4A viewed along section line 4B—4B.
Figure 4A:
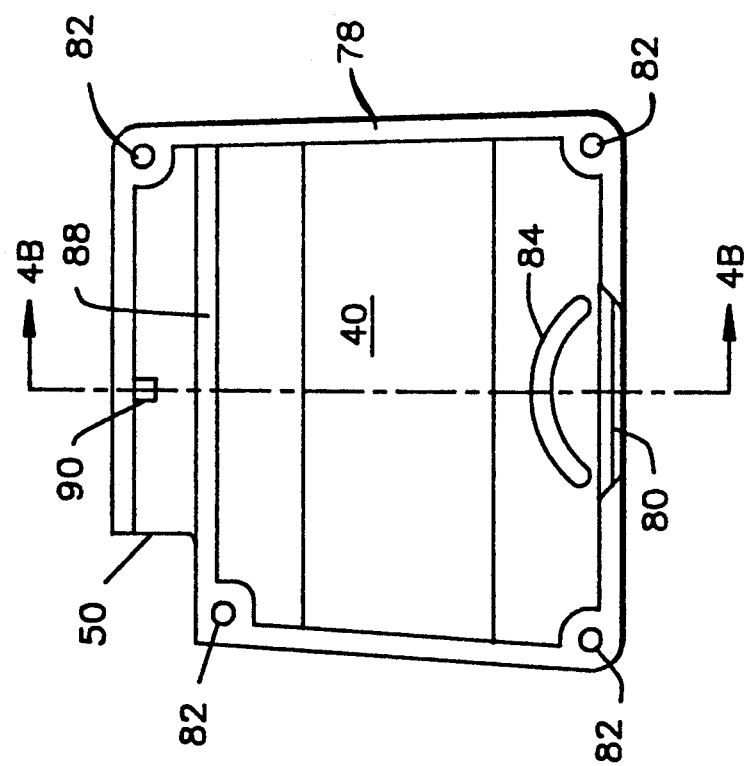
FIG. 4A is a side view depicting the interior of the opposing half of the housing of the present invention.

Referring to FIGS. 4A and 4B there is shown the interior of the second half 40 of the lancet housing 16 and a cross-sectional view of that second half 40 respectively. As with the first housing half 38, the second housing half 40 is for the most part hollow having a periphery defined by an edge wall 78. The edge wall 78 is not continuously formed around the second housing half 40, but rather is disrupted in one corner to form the second half of the aperture 50 through which the trigger plunger 14 will pass. Similarly, the edge wall 78 has a reduced section 80 along its bottom edge. The reduced section 80 forms the second half of the elongated slot 44 through which a cutting blade will extend.

Positioned at four points proximate the four corners of the second housing half 40 are dowel pins 82. The dowel pins 82 correspond in position to the dowel holes 54 formed on the first housing half 38 thereby allowing the dowel pins 82 to enter the opposing dowel holes 54 when the first housing half 38 is joined to the second housing half 40 and the housing 16 is assembled. An arcuate protrusion 84 extends from the inner surface of the front housing half above the reduced section 80 of the bottom surface edge wall. As will be later explained, the arcuate protrusion 84 acts as a spacer which helps hold the cutting blade in a desired cutting path.

A second support track 88 is formed at the upper end of the second housing half 40. The second support track 88 corresponds in position to the first support track 62 of the first housing half 38. As such, the second support track 88 cooperates with the first support track 62 to support and guide the movement of the trigger plunger 14 in the housing 16. A stop tab 90 is positioned at a point above the support track 88. The stop tab 90 engages the trigger plunger 14, preventing the trigger plunger from being removed from the assembled housing 16.

Referring to FIGS. 5A, 5B and 5C there is shown one preferred embodiment of a pivot arm member 92 and corresponding cutting blade 104. The shape of the pivot arm member 92 is essentially that of a tear drop having trigger hook projection 98 extending from its top edge. An aperture 100 is formed through the pivot arm member 92 at a point proximate trigger hook projection 98. As will later become apparent, the aperture 100 allows a spring to engage and move the pivot arm member 92. A blade retaining relief 102 is formed at the distal end of the pivot arm member 92, opposite the trigger hook projection 98. The blade retaining relief 102 retains a blade 104 onto the pivot arm member 92 allowing the cutting edge 106 of the blade 104 to extend down from the pivot arm member 92 at an angle substantially perpendicular to the bottom of the pivot arm member 92. The blade retaining relief 102 may be a slot into which the blade 104 is press fit, however, other conventual means can be used to retain the blade 104, such as gluing and the like.

Three spacer posts 108 extend from one side of the pivot arm member 92. The spacer posts 108 contact the inside surface of the housing 16 when assembled within the housing 16. As such, the spacer posts 108 help prevent the pivot arm member 92 from moving in any undesired direction during the operation of lancet device 10. On the side of the pivot arm member 92 opposite the space posts 108 is formed a U-shaped channel 110. The open end of the U-shaped channel 110 is directed at the bottom most surface of the pivot arm member 92 from which the cutting edge 106 of the blade 104 extends. A cam follower 112 extends from the side of the pivot arm member 92 containing the U-shaped channel 110. As will later be explained, the cam follower 112 is sized to fit within the cam guide channel 68 of the first housing half 38, whereby the movement of the pivot arm member 92 in the housing 16 depends largely on the movement of the cam follower 112 through the cam guide channel 68.

In FIG. 6A and 6B there is shown the preferred embodiment of the trigger plunger 14 having a flush finger tab 20 formed at one end which leads into a pushrod 22. On the lower end of the pushrod 22, proximate the finger tab 20 are indentations 32 that the safety clip 26 engage. Reliefs 114 are formed on either side of the pushrod 22. The reliefs 114 are formed to accept the stop tabs 64, 90 formed on the two halves of the housing 16. The stop tabs 64, 90 limit the movement of the trigger plunger 14 as will be later explained. The region of the trigger plunger 14 proximate its distal end 118 is angled downwardly, thereby giving the trigger plunger 14 a substantially J-shaped profile. A supporting rib 120 extends from the pushrod 12 to the region proximate the distal end 118 as to provide support and rigidity to the distal end 118.

Figure 7A:
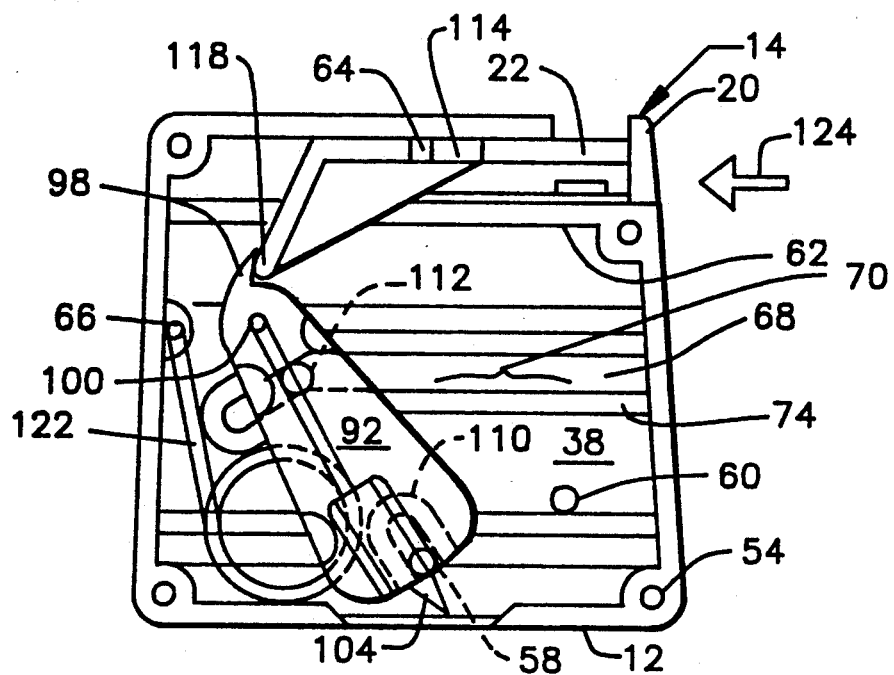
FIG. 7A, 7B and 7C show a partial assembly view of one preferred embodiment of the present invention as it would appear at three different points during it's operation.

Referring now to FIG. 7A a partially assembled lancet device 10 is shown wherein the trigger plunger 14, pivot arm member 92 and a spring 122 are assembled into the first housing half 38. As can be seen, the trigger plunger 14 rests upon the support track 62 formed on the first housing half 38. The support track 62 thereby acts as guide for the trigger plunger 14, allowing the trigger plunger 14 to move reciprocally within the housing. However, the stop tab 64 protruding from the first housing half 38 above the support track 62, extends into the relief 114 formed on the trigger plunger 14. Since the edges of the relief 114 contact stop tab 64, the length of the relief 114 determines the range of travel permitted by the trigger plunger 14. In FIG. 7A the lancet device 10 is shown in its unused position. As such, the stop tab 64 contacts the edge of the relief 114 opposite the finger tab 20. This contact prevents the trigger plunger 14 from being pulled out of the housing. It should be understood that although only the first half 38 of the housing 16 is shown, that the trigger plunger 14 is supported in a similar manner by the second half 40 of the housing 16. Before the lancet device 10 is ready to be used the safety clip 26 (See FIG. 1) is positioned around the pushrod 22 of the trigger plunger 14 that extends from the housing. As can be seen, the safety clip 26 contacts both the fingertab 20 and the housing, thereby preventing the trigger plunger 14 from being advanced into the housing until the safety clip 26 (See FIG. 1) is removed.

When the pivot arm member 92 is assembled into the lancet device 10, the pivot arm member 92 is positioned into the first half 38 of the housing 16 such that the cam follower 112 of the pivot arm member 92 enters the cam guide channel 68 protruding from the first housing half 38. Similarly, the pivot pin 58 extending from the first housing half 38 enters the U-shaped channel 110 on the pivot arm member 92. Before the lancet device 10 is used, the pivot arm member 92 that holds the blade 104 is set into a spring biased position, so as to provide the needed energy for the cutting action. In the preferred embodiment, the spring bias is provided by a torsional wire spring 122, however, it should be understood that any other spring such as a tension spring or a leaf spring may also be used. The torsional wire spring 122 has two ends that are based apart. The first end of the torsional wire spring 122 is held within the spring anchor aperture 66 that is formed in the first half 38 of the housing 16. The second end of the torsional were spring 122 is held within the aperture 100 formed through the pivot arm member 92. As such, when the pivot arm member 92 is advanced to the left of the housing and the two ends of the torsional wire spring 122 approach each other, greater amounts of energy are stored on within the torsional wire spring 122.

Before the lancet device 10 is used, the trigger hook projection 98 on the arm member 92 engages the distal end 118 of the trigger plunger 14. In this set position, the two ends of torsional wire spring 122 are biased near one another and energy is stored within the torsional wire spring 122. In this set position, the cam follower 112 on the pivot arm member 92 is positioned within cam guide channel 68 of the first housing half 38 at a point proximate where the long straight section 70 of the cam guide channel 68 changes the short curved descending section 72. Furthermore, at this set position the pivot pin 58 on the rear housing half 38 is positioned within the U-shaped channel 110 of the pivot arm member 92 at a point proximate the open end of the U-shaped channel 110. To operate the lancet device 10, the safety clip 26 is removed and the trigger plunger 14 is depressed into the housing, as indicated by arrow 124. The depression of the trigger plunger 14 into the housing makes the pivot arm member 92 move further to the left and further compresses the torsional wire spring 122. The movement of the pivot arm member 92 is controlled by the cam follower 112 of the pivot arm member 92 following the cam guide channel 68 on the first housing half 38. As the trigger plunger 14 is depressed and the pivot arm member 92 moves to the left in the housing, the cam follower 112 travels into the short curved descending section 72 of the cam guide channel 68. The curvature of the short descending section 72 allows the cam follower 112 to traverse the short descending section 72 without effecting the relative position of the pivot pin 58 in the U-shaped channel 110. As such, the pivot arm member 92 pivots around pivot pin 58 until the trigger hook projection 98 of the pivot arm member 92 descends and no longer engages the distal 118 of the trigger plunger 14. Once the trigger hood projection 98 clears the distal end 118 of the trigger plunger 14, the pivot arm member 92 is free to move under the influence of the torsional wire spring 122. As a consequence of the energy stored within the torsional wire spring 122, the pivot arm member 92 is rapidly moved to the right. The cam follower 112 therefore rapidly exits the short descending section 72 of the face cam channel 68 and begins traversing the long straight section 70 of the face cam channel 68 from the left to right.

Figure 7B:
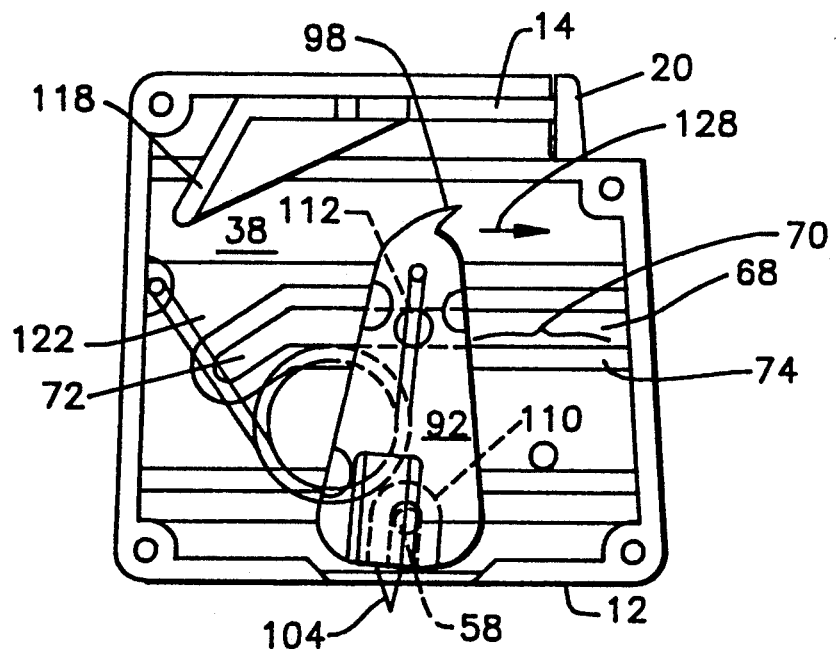

Referring to FIG. 7B, the present invention lancet device 10 is shown at a point where the trigger plunger 14 has been depressed and the pivot arm member 92 has traveled half-way across the cam guide channel 68. As can be seen, the energy stored within the torsional wire spring 122 is causing the pivot arm member 92 to pivot about pivot pin 58 and travel in the direction of arrow 128. The movement of the pivot arm member 92 is controlled by the presence of the cam follower 112 in the face cam channel 68 and the presence of the pivot pin 58 in the U-shaped channel 110 on the pivot arm member 92. As will be recognized by a person skilled in the art, the distance between the pivot pin 58 and the cam guide channel 68 varies across the length of the face cam channel 68. Since the pivot arm member 92 engages both the pivot pin 58 and the face cam channel 68, as the pivot arm member 92 travels along the cam guide channel 68 the distance between the cam follower 112 and the pivot pin 58 varies. The pivot pin 58 is engaged by the U-shaped channel 110 formed on the pivot arm member 92. The U-shaped channel 110 is elongated and as such, is able to travel back and forth and pivot about in axis upon the pivot pin 58. The reciprocal movement of the U-shaped channel about the pivot pin 58, thereby provides the unique and necessary combination of guidance and trajectory for the projected blade 104 as dictated by the cam follower 112 as it travels across the length of the face of the cam guide channel 68.

In FIG. 7B, the present invention lancet device 10 is shown where the cam follower 112 of the pivot arm member 92 is positioned within the face cam channel 68 at a point substantially above the pivot pin 58. Due to the shape of the face cam channel 68, the pivot arm member 92 is forced downwardly in the housing 16 as the cam follower 112 traverses the center region of cam guide channel 68. As such, the U-shaped channel 110 of the pivot arm member 92 is driven to a point of maximum engagement about pivot arm 58 and blade 104 protruding from the bottom of the pivot pin member 92 is driven out of the housing 16 through the elongated slot 44 on the bottom edge 12 of the housing.

Figure 7C:
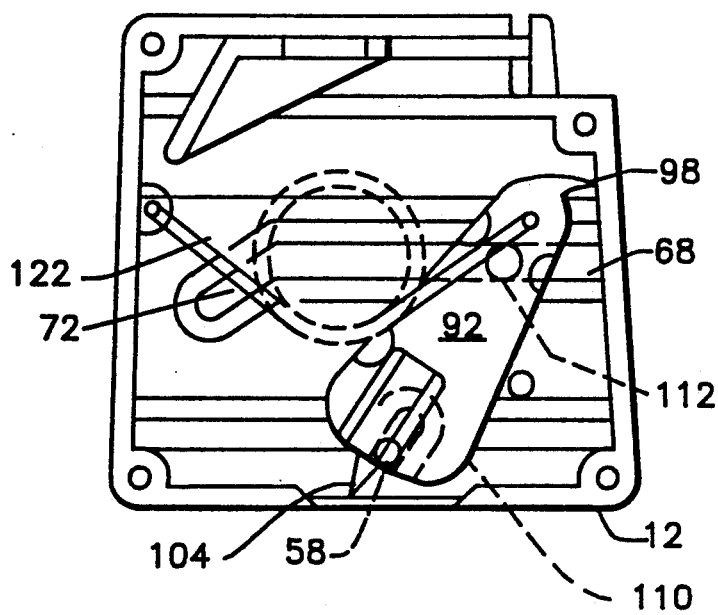

Referring to FIG. 7C, the present invention lancet device 10 is shown wherein the torsional wire spring 122 has biased the pivot arm member 92 to a point where the pivot arm member 92 now contacts a side wall of the housing 16. At this point, the cam follower 112 of the pivot arm member 92 has traveled within the cam guide channel 68 to a point near the right edge of the housing 16. Consequently, the distance between the pivot pin 58 and the cam follower 112 has been increased over the shown position of FIG. 7B. The shape of the face cam follower 112 thereby elevates the position of the pivot arm member 92 in the housing 16. As such, the U-shaped channel pivot arm member 92 is drawn to a point at minimum engagement on the pivot arm 58 and the blade 104 is retracted back into the housing 16.

The movement of the pivot arm member 92 from the loaded position of FIG. 7A to the spent position of FIG. 7C is a one-time-use operation and may be made extremely rapidly as determined by the strength of the torsional wire spring 122. Thus, the blade 104 may be projected form the slot 144 in the bottom of the housing 16 in an extremely short period such as a fraction of a second. The patient's awareness of the incision process is minimized by the rapid cutting action and pain is reduced by the slicing action of the blade 104 which will be later described.

Figure 8:
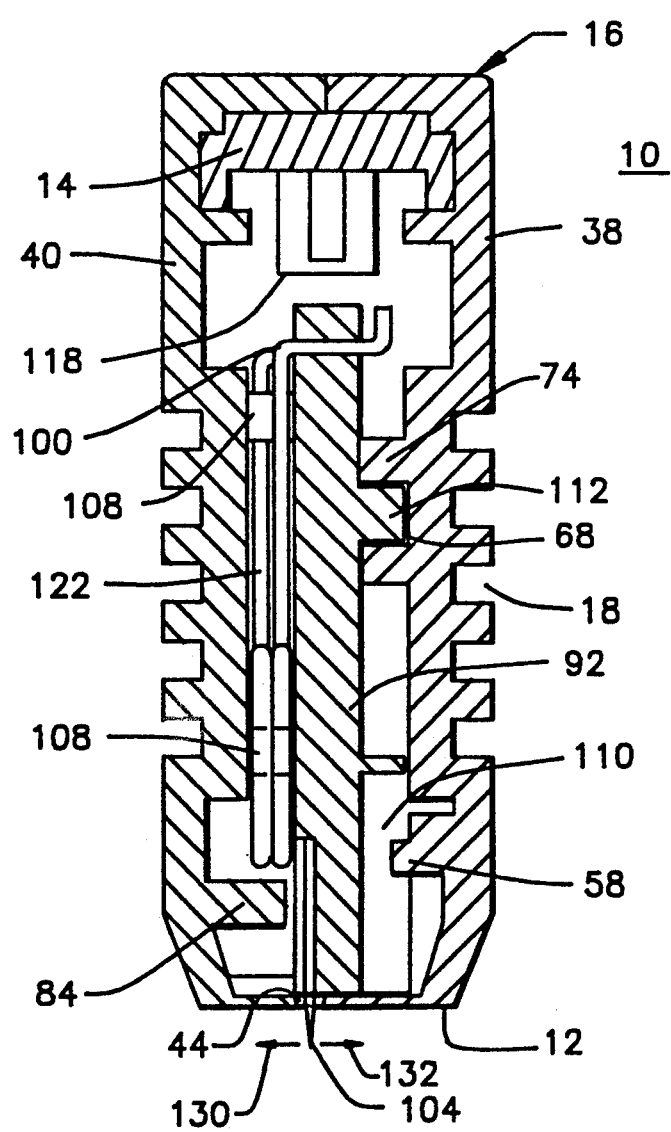
FIG. 8 is a partial assembly view of one preferred embodiment of the present invention showing the range movement produced in the cutting blade.

In FIG. 8, there is shown a cross sectional view of the present invention lancet device 10 during the cutting operation. As will be understood by a person skilled in the art, it is highly desirable to create a perfectly linear incision in a patent so as to minimize tissue damage in the areas surrounding the incision. In other words, it is highly desirable to minimize the travel of the blade in the directions of arrows 130 and 132 during the operation of the lancet device 10. In the prior art devices, there is inevitably a small degree of wobbling that occurs in the path of the blade as it creates an incision in a patent. This wobble causes inconsistencies along the edges of the incision which effect the surrounding tissue and make it harder for the incision to heal. Referring to FIG. 8, it can be seen that as the cam follower 112 on the pivot arm member 92 rides within the cam guide channel 68, the top edge of the flange walls 74 that create the cam guide channel 68 abut against the pivot cam member 92. Similarly, as the pivot pin 58 rides within the U-shaped channel 110 on the pivot arm member 92, the top edges of the U-shaped channel 110 abut against the first half 38 of the housing 16. The contact between the pivot arm member 92 and the first half 38 of the housing 16 prevents any movement of the pivot arm member 92 toward the first half 38 of the housing 16 during the incision operation.

As has been previously mentioned, a plurality of spacer posts 108 are positioned on the pivot arm member 92 on the opposite side of the cam follower 112 and U-shaped member 110. The spacer posts 108 abut against the second half 40 of the housing 16 during the operation of the lancet device 10. Similarly, the protrusion 84 that extends from the second half 40 of the housing 16 abuts against the pivot arm member 92. The combined contact between the pivot arm member 92 and both the arcuate protrusion 84 and spacer posts 108 prevents any movement of the pivot arm member 92 toward the second half 40 of the housing 16 during the incision operation. Since the pivot arm member 92 is restrained from moving toward either half of the housing 16 during the incision of operation, the blade 104 is assured of traveling in a single plane, thereby following a linear path and creating a clean incision.

Figure 9:
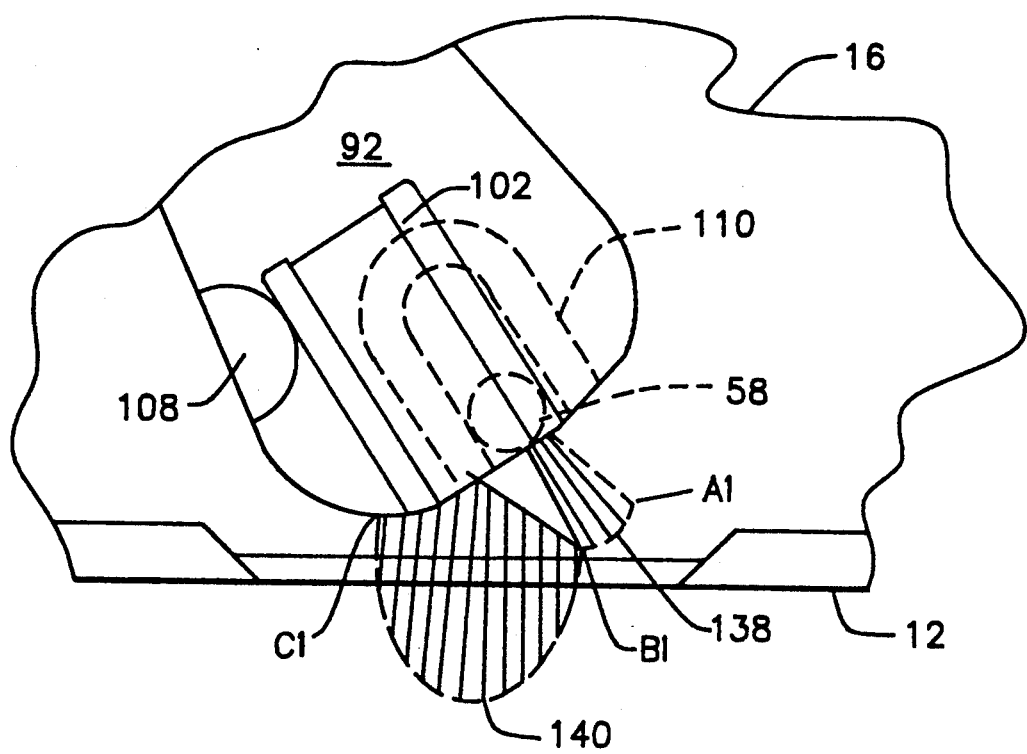
FIG. 9 is an enlarged partial view depicting the trajectory of the blade according to this invention.

In FIG. 9, the shape of the incision made by the blade 104 into the tissue of a patient is shown. Referring to FIG. 9, in combination with FIGS. 7A-7C the position of the blade 104 at various points during the operation of the lancet device 10 will be described. From FIG. 9 it can be seen that the blade 104 follows two curves during the operation of lancet device 10. The first curve 138 extends from point A1 to point B1 and is created when the cam follower 112 attached to the pivot arm member 92 is positioned within the short descending section 72 of the cam guide channel 68. As can be seen, the blade 104 following the first curve 138 does not extend out below the bottom edge 12 of the lancet device 10. As a result, it should be understood that while the cam follower 112 is within the short descending section 72 of the cam guide channel 68 no part of the incision can occur. Point B1 is the transition point between the first curve 138 and a second curve 140, which extends from point B1 to point C1. The second curve 140 is substantially tear drop in shape, descending well below the bottom edge 12 of the lancet device 10. Point B1 corresponds to the transition point between the short descending section 72 and the long straight section 70 of the cam guide channel 68. That is, when the cam follower 112 of the pivot arm member 92 is at the transition point between the short descending section 72 and long straight section 70 of the cam guide channel 68, the point of the blade 104 is positioned at point B1 in between the first curve 138 and the second curve 140. As the cam follower 112 of the pivot arm member 92 traverses the long straight section 70 of the cam guide channel 68, the blade 104 follows the path of the second curve 140 from point B1 to point C1. As can be seen from FIG. 9, as the blade 104 follows the path of the second curve 140 the blade 104 protrudes from the housing 16 of the lancet device 10 and is eventually again retracted into the housing 16. The blade 104 does not plunge into the tissue of a patient. Rather, as the blade 104 follows the path of the second curve 140 there is both an X and Y component to the movement of the cutting edge 106. Consequently, the blade 104 slices the tissue of the patient, traversing across the tissue of the patient as the blade 104 descends into, and ascends from, the tissue of the patient. The blade 104 is thereby allowed to cause a deep narrow cut into the patient's tissue without the adverse effects of just plunging a blade directly into the patient.

The present invention lancet device 10 creates a short yet deep incision into the tissue of a patient using a slicing cutting action, thus creating an incision that is substantially painless with reduced trauma to the surrounding tissue of the patient. The present invention lancet device 10 has the further advantage of being inexpensive to fabricate, since all parts can be made from plastic, with exception to the cutting blade and spring.

It will be understood that the embodiment described herein is merely exemplary and that a person skilled in the art may make many variations and modifications to the described embodiment utilizing functionally equivalent elements to those described. More specifically, it should be understood that any spring bias means can be used in place and stead of the torsional wire spring described. Additionally, dimensions and proportions of interrelating parts can be altered to effect incision of differing lengths and depths. All such variations and modifications are intended to be included within the scope of this invention as defined by the append claims.

What is claimed is:

1. A lancet device for implementing an incision comprising;
   a hollow housing means having at least two opposing internal surfaces;
   a pivot arm supporting a blade located within said housing means;
   biasing means for biasing said pivot arm from a first position to a second position within said housing means;
   a guide means within said housing means for guiding the path of said pivot arm from said first position to said second position, said guide means causing said blade to emerge from said housing means, create said incision with a slicing motion and return into said housing means wherein said blade follows a generally tear drop shaped path between said first position and said second position; and
   a contact means for creating contact between said pivot arm said two opposing internal surfaces as said pivot arm moves from said first position to said second position, said contact means limiting the movement of said blade support arm and said blade to a single plane.

2. The lancet device of claim 1, wherein said contact means includes at least one spacing member formed on said pivot arm, said at least one spacing member contacting and wiping across at least one of said internal surfaces of said housing means as said pivot arm travels from said first position to said second position, the contact between said at least one spacing member and said at least one internal surface confining the movement of said pivot arm to a single plane.

3. The lancet device of claim 2, wherein said contact means includes at least one spacer formed on at least one internal surface of said housing means, said at least one spacer contacting and wiping across said pivot arm as said blade support arm travels from said first position to said second position, the contact between said at least one spacer and said pivot arm confining the movement of said pivot arm to a single plane.

4. The lancet device of claim 1, wherein said guide means includes a slot receptacle formed on said pivot arm, said slot receptacle engaging a pivot pin extending from said housing means wherein said pivot pin can move reciprocally with said slot receptacle as said pivot arms pivots around said pivot pin from said first position to said second position.

5. The lancet device of claim 4, wherein said guide means includes a projection formed on said pivot arm, said projection engaging in a groove formed on at least one of said internal surfaces of said housing, said groove guiding the movement of said projection as said pivot arm moves from said first position to said second position, the shape of said groove determining the reciprocal motion of said pivot pin relative said slot receptacle.

6. The lancet device of claim 5, wherein said groove is substantially J-shaped having a long linear section that terminates at one end in a relatively short curved section.

7. The lancet device of claim 6, wherein said projection formed on said pivot arm is positioned within said curved section of said groove when said pivot arm is in said first position, said projection traversing said curved section and said linear section of said groove when said blade support arm travels from said first position to said second position.

8. The lancet device of claim 7, further including a trigger means for selectively controlling the movement of said pivot arm from said first position to said second position.

9. The lancet device of claim 8, further including a safety means removably affixed to said trigger means for preventing the inadvertent activation of said trigger means.

10. A lancet device for implementing an incision comprising:
- a hollow housing means having two substantially parallel opposing internal surfaces wherein a groove having a linear section is located on at least one of said internal surfaces and a pivot pin extends from one of said internal surfaces into the hollow of said housing means;
- a pivot arm pivotably secured within said housing means, said pivot arm having a projection movably engaging said groove;
- a biasing means for biasing said pivot arm to enable said pivot arm to move from a first position to a second position thereby causing said projection to traverse said linear section of said groove; and
- a blade affixed to said pivot arm, said blade emerging from said housing means and creating said incision with a slicing motion, said slicing motion being controlled by said projection engaging said linear section of said groove as said pivot arm travels from said first position.

11. The lance device of claim 10, further including a contact means for creating contact between said pivot arm and said opposing internal surfaces in said housing as said pivot arm travels from said first position to said second position the contact between said contact means and said opposing internal surfaces limiting the movement of said pivot arm to a single plane.

12. The lance device of claim 11, wherein said blade follows a substantially tear drop shaped path as said pivot arm moves from said first position to said second position and said projection traverses said linear section of said groove.

13. The lance device of claim 12, wherein said contact means includes at least one spacing member formed on said pivot arm, said at least one spacing member contacting and wiping across at least one of said opposing internal surfaces as said pivot arm travels from said first position to said second position, said contact means confining the movement of said pivot arm to a single plane.

14. The lancet device of claim 13, wherein said contact means includes at least one spacer formed on at least one internal surface of said housing means, said at least one spacer contacting and wiping across said pivot arm as said pivot arm, travels from said first position to said second position, the contact between said at least one spacer and said pivot arm confining the movement of said pivot arm to a single plane.

15. The lancet device of claim 14, wherein the movement of said projection in said linear section of said groove, as said pivot arm travels from said first position to said second position causes said blade to emerge from said housing means implement said incision and be retracted back into said housing means.

16. The lancet device of claim 15, wherein a slot receptacle is formed on said pivot arm, said slot receptacle engaging a pivot pin extending from said housing means creating a pivotable connection, and wherein said pivot pin moves reciprocally within said slot receptacle of said projection as said pivot arm traverses said linear section of said groove.

17. The lancet device of claim 16, further including a trigger means for selectively controlling the movement of said pivot arm from said first position to said second position.

18. The lancet device of claim 17, further including a safety means removeably affixed to said trigger means for preventing an inadvertent actuation of said trigger means.

* * * * *